(12) United States Patent
Doneskey

(10) Patent No.: US 12,714,594 B2
(45) Date of Patent: Aug. 25, 2026

(54) ADJUSTABLE ORAL APPLIANCE

(71) Applicant: RespiraWorks, LLC, Spokane, WA (US)

(72) Inventor: Jeffrey W. Doneskey, Bellevue, WA (US)

(73) Assignee: RespiraWorks, LLC, Spokane, WA (US)

( * ) Notice: Subject to any disclaimer, the term of this patent is extended or adjusted under 35 U.S.C. 154(b) by 182 days.

(21) Appl. No.: 18/403,640

(22) Filed: Jan. 3, 2024

(65) Prior Publication Data

US 2024/0216165 A1 Jul. 4, 2024

Related U.S. Application Data

(60) Provisional application No. 63/539,015, filed on Sep. 18, 2023, provisional application No. 63/457,540, filed on Apr. 6, 2023, provisional application No. 63/436,848, filed on Jan. 3, 2023.

(51) Int. Cl.
*A61F 5/56* (2006.01)
*A61C 7/08* (2006.01)
*A61C 7/36* (2006.01)

(52) U.S. Cl.
CPC ................ *A61F 5/566* (2013.01); *A61C 7/08* (2013.01); *A61C 7/36* (2013.01)

(58) Field of Classification Search
CPC ...... A61F 5/566; A61F 5/56; A61F 2005/563; A61C 7/008; A61C 7/08; A61C 7/10; A61C 7/36; A61C 7/002
See application file for complete search history.

(56) References Cited

U.S. PATENT DOCUMENTS 5,755,219 A * 5/1998 Thornton .......... A61M 16/0493 128/201.18
6,109,265 A * 8/2000 Frantz ..................... A61F 5/566 128/862

(Continued)

FOREIGN PATENT DOCUMENTS

EP 3 103 420 8/2017

OTHER PUBLICATIONS

Sommondent: Avant: Source: website: https://somnomed.com/au/patients/products/somnodent/somnodent-avant/ Website Owner: Somnomeds.com.

*Primary Examiner* — Camtu T Nguyen
(74) *Attorney, Agent, or Firm* — WORKMAN NYDEGGER

(57) ABSTRACT

An oral appliance with an upper tray, a lower tray, and a flat cord that extends around and slides freely in a receiving slot formed on the front surface of the upper tray. The opposite ends of the flat cord extend diagonally rearward and connect to side connectors on the lower tray's outside surfaces of the two wing sections. The flat cord is made of non-elastic material, so it maintains its original length during use. During use, the flat cord self-adjusts its position over the upper tray to pull the wing sections on the lower tray forward relative to the upper tray evenly. A spacer may be formed on the abutting front curved surfaces of the front or lower trays to hold the trays' wing sections apart. The appliance may be distributed with a set of cords with different lengths that apply different pulling forces on the lower tray.

11 Claims, 15 Drawing Sheets

(56) References Cited

U.S. PATENT DOCUMENTS

| | | | | |
|---|---|---|---|---|
| 6,983,752 | B2 * | 1/2006 | Garabadian | A61F 5/566<br>128/848 |
| 7,637,262 | B2 * | 12/2009 | Bailey | A61F 5/566<br>433/7 |
| 7,810,502 | B1 * | 10/2010 | Nguyen | A61F 5/566<br>128/859 |
| 9,498,373 | B2 * | 11/2016 | Scheffel | A61C 11/00 |
| 11,911,235 | B2 * | 2/2024 | Hofmann | A61C 7/08 |
| 2023/0065574 | A1 * | 3/2023 | Gergen, II | A61F 5/566 |

* cited by examiner 55
52
12
58
21
20
56
50
54
53

25
34
50
52

52
53
62
60
63

13
20
21
14
12
19

52
53
62
60
63

160
122
120
12
150

120
150
123
122

ADJUSTABLE ORAL APPLIANCE

REFERENCES TO RELATED APPLICATIONS

This utility patent application is based on U.S. Provisional Patent Applications filed on Sep. 27, 2023 (Application No. 63/539,015); Apr. 6, 2023 (Application No. 63/457,540) and Jan. 3, 2023 (Application No. 63/436,848).

BACKGROUND OF THE INVENTION

1. Field of the Invention

This invention relates to dental appliances used to treat sleep apnea and, more particularly, to appliances that self-adjust or self-balance to the user's oral cavity.

2. Description of the Related Art

Oral appliances are commonly used to treat sleep apnea. They include upper and lower trays that fit around the maxillary and mandibular arches while the person sleeps. The two trays are coupled to pull the lower tray and the mandibular arch forward with respect to the upper tray and the maxillary arch. The goal is to hold the lower tray forward in a comfortable resting position while the user sleeps.

Several patents for sleep apnea oral appliances that use upper and lower trays over the maxillary and mandibular arches that hold the mandibular arch forward while sleeping have been granted. These patents teach different mechanisms, such as elastic cords, fins, screw mechanisms, etc., that advance and hold the lower jaw forward relative to the upper jaw.

An ideal sleep apnea oral appliance should be designed to prioritize comfort for users while effectively addressing the underlying issue of sleep apnea. The different mechanisms that use elastic cords or screw mechanisms have drawbacks, particularly in terms of causing discomfort for patients.

Patients often complain of discomfort when sleep apnea oral appliances use two cords attached to the opposite sides of the lower tray. The two cords create different pulling forces on the lower tray, causing an imbalance that can cause discomfort. In addition, patients often complain about imbalances from right to left in the molar regions of the appliances that also cause discomfort during use. One innovative solution could incorporate a cord system between the upper and lower trays, incorporating a dynamic, self-adjusting mechanism and the use of a spacer that keeps the molar region apart when the appliance is worn. A self-adjusting mechanism that responds to the user's natural jaw movements during sleep, ensuring that the forces applied between the upper and lower trays remain balanced and comfortable.

To further enhance user satisfaction, the sleep apnea oral appliance could incorporate user-friendly features such as a quick-release mechanism for easy removal and cleaning. Customization options, such as adjustable settings for the degree of mandibular advancement, would provide flexibility to cater to the unique anatomical variations among users.

In summary, the key to an improved sleep apnea oral appliance lies in a thoughtful design that effectively addresses the physiological aspects of sleep apnea and prioritizes user comfort.

SUMMARY OF THE INVENTION

It is an object of the present invention to provide an oral appliance used to treat sleep apnea or snoring that uses an upper and lower tray configured to fit over the maxillary and mandibular arches, respectively, that uses a cord system that is self-adjusting and 'balances' the forces exerted on the two trays that hold the mandibular arch and lower tray forward relative to the maxillary arch and upper tray during sleep. The term 'balances' refers to the two equal pulling forces exerted on the opposite wing sections of the lower tray relative to the upper tray. The formation of a space is maintained between the posterior surfaces of the wing sections on the upper and lower tray.

Another objective is to provide an oral appliance that enhances comfort, reduces instances of jaw and muscle pain, and requires minimal adjustments by the user or clinician.

The sleep apnea oral appliance disclosed herein includes an upper tray configured to fit around the maxillary arch and a lower tray around the mandibular arch. A slot is formed or attached to the upper tray. In one embodiment, a slot is formed in a separate structure, called a guide member, attached to the upper tray's vertical front surface. Another embodiment involves the slot being directly formed on the front surface of the upper tray. In both embodiments, the slot captures the middle section of a single cord that is circular in cross-section. The cord extends downward and connects at its opposite ends to side connectors attached or formed on opposite wing sections on the lower tray. In one embodiment, the cord may include optional stop elements designed to press against the side of the guide member and stop excessive cord sliding on the guide member.

In another embodiment, the slot is formed on a guide member formed or attached to the bottom surface of the upper tray. The guide member extends downward from the upper tray. Using a guide member attached to the bottom surface of the upper tray reduces the diagonal angle of the cord. The guide member also creates and maintains an open space or air gap between the adjacent surfaces of the upper and lower trays. Also, because the guide member extends downward from the upper tray, irritation caused by the guide member against the user's lips and buccal mucosa is eliminated.

In another embodiment, the oral appliance includes a thin, forward extension clip on the front curved surface of the upper tray. Located inside the clip is a vertical groove or slot. This embodiment uses a flat cord that slides freely back and forth in the slot. Like the round cord used in the other embodiments, the flat cord includes two end connectors formed or attached at the cord's opposite ends that selectively connect to two side connectors mounted on the outside surfaces of the lower tray's two wing sections. The dimensions of the end connectors are configured so that the flat cord fits through the slot. The front surface of the upper tray is also slanted rearward so that the flat cord's longitudinal axis is substantially perpendicular to the front surface of the upper tray, and the flat cord's inside surface rests against the front curved surface of the upper tray.

The round and flat cord are made of lightweight material, such as plastic or nylon, resistant to stretching.

In all embodiments, side connectors are mounted on the lower tray's lateral surfaces near the lower tray's wing sections. During use, the side connectors connect to compatible end connectors attached to the opposite ends of the cord. In one embodiment, the side connectors have tabs, and the end connectors have compatible offset keyways. The end connectors must be rotated 90 degrees when connecting and disconnecting the end connectors to the side connectors.

Additionally, each embodiment may feature an optional spacer on either the bottom surface of the front curved section of the upper tray or the top surface of the front curved section on the lower tray. The spacer is axially aligned with the front curves section on the upper or lower tray. The height of the spacer is sufficient in height so that the posterior wing sections of the upper and lower trays are spaced apart when worn. In different embodiments, the spacer has a convex surface. The side-to-side dimension of the spacer is short so that an airway is maintained between the upper and lower trays when worn.

To treat sleep apnea, the user selects a cord configured to apply light forces to the opposite sides of the lower tray so that the lower tray is pulled and held anteriorly relative to the upper tray. If the forces exerted on opposite sides of the lower tray are insufficient or causes discomfort, a cord may be replaced by a different length cord.

DESCRIPTION OF THE PREFERRED EMBODIMENT(S)

Figure 1:
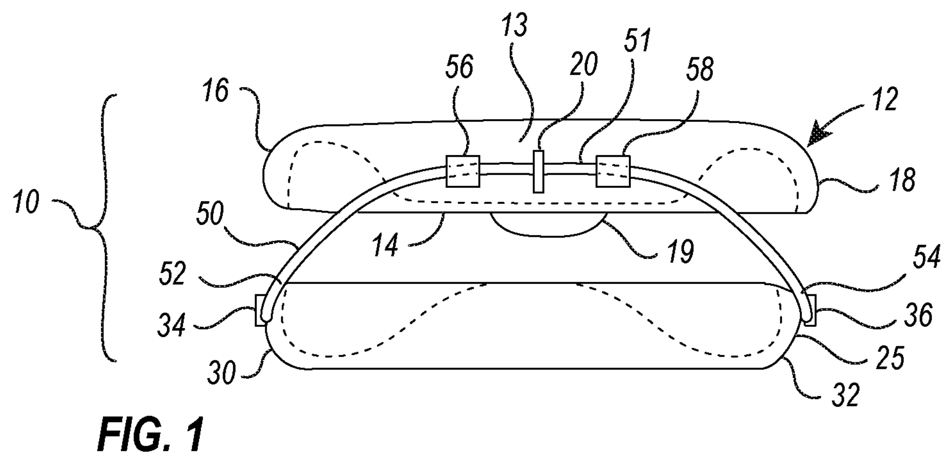
FIG. 1 is a front elevation view of an oral appliance with an upper tray and a lower tray, coupled together with a cord that fits through a guide member mounted on the upper tray's front surface and has two opposite ends that attach to connectors mounted on the lateral surface of the lower tray near the lower trays' posterior wing sections.

Referring to the FIGS., an oral appliance 10 is shown used to treat sleep apnea or snoring that uses an upper tray 12 and a lower tray 25 configured to fit over the maxillary and mandibular arches, respectively. The upper tray 12 includes a curved front surface 13, a curved bottom surface 14 and two opposite posterior wing sections 16, 18. The lower tray 25 also includes a curved front surface 26, a curved top surface 28, and two opposite posterior wing sections 30, 32. Coupling the two trays 10 and 12 is a single cord 50 configured to pull the lower tray 25 forward with sufficient force ‘f’ when sleeping to reduce or stop sleep apnea.

Figure 2:
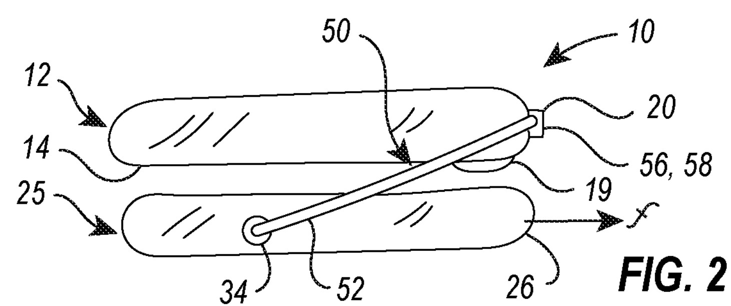
FIG. 2 is a sectional side elevation view of the oral appliance shown in FIG. 1.

The cord 50 includes a middle section 51, and two opposite end sections 52 and 54. The cord 50 is sufficient in length to extend around the curved front surface 13 of the upper tray 12, and its opposite ends bend rearward and downward, as shown in FIG. 2, to engage the end connectors 34 and 36 mounted on the outside surfaces of the lower tray 25.

In this embodiment, guide member 20 is mounted on the front surface 13 of the upper tray 12. Formed in the guide member 20 is a slot configured to capture cord 50. Hole 21 is slightly larger than cord 50, allowing cord 50 to side transversely over the upper tray's front surface 13. In the embodiment shown, one guide member 20 is used and aligned over the upper tray's center axis. Two or more guide members 20 may be used on the front surface 13. It should also be understood that on guide member 20, slot 21 may be replaced with a hole or groove formed on the front surface 13 of the upper tray 12.

Figure 3:
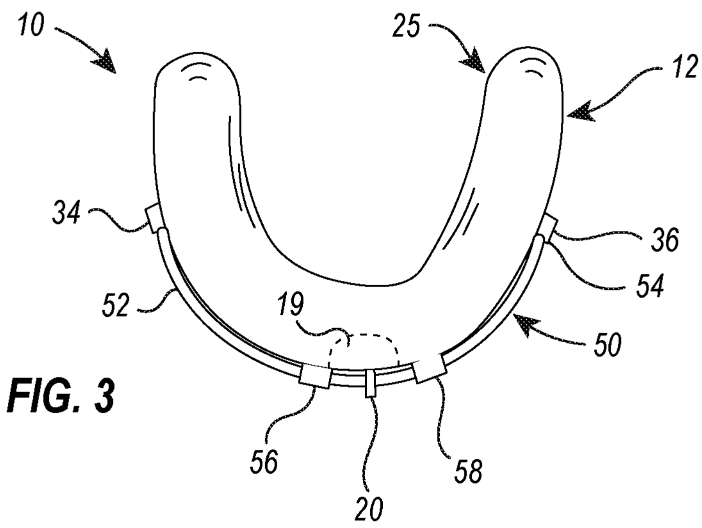
FIG. 3 is a top plan view of the oral appliance shown in FIGS. 1 and 2.
Figures 4, 5, 6, 7, 8:
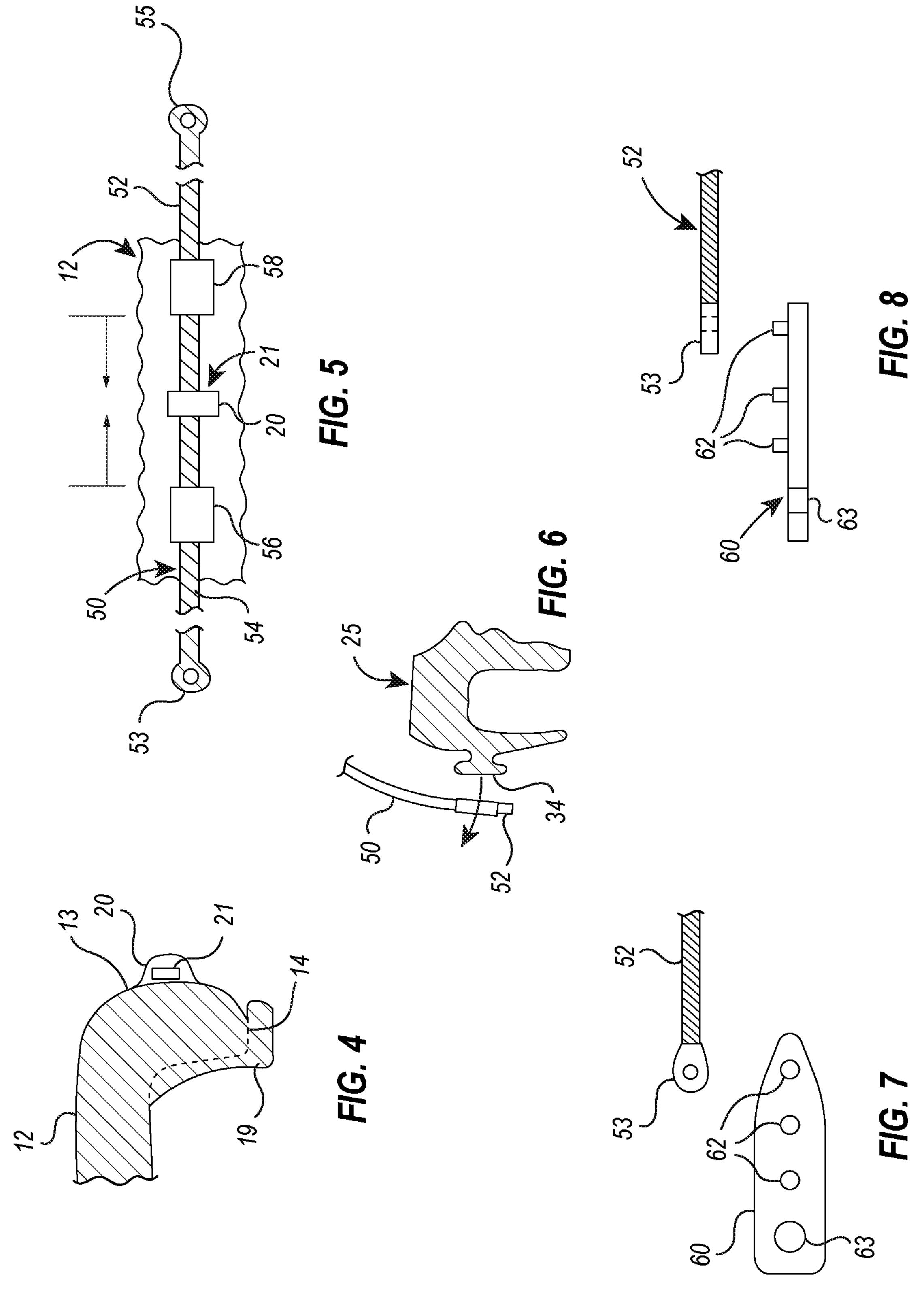
FIG. 4 is a sectional side elevation view of the upper tray with a guide member mounted on the front surface.
FIG. 5 is an enlarged, partial front elevation view of the upper tray showing the cord with two stops spaced apart on the cord and opposite sides of the guide member.
FIG. 6 is a partial, sectional view of the lower tray near one of its posterior wing sections with a side connector extending outward from the lateral surface.
FIG. 7 is a top plan view of an optional extension that attaches at one end to the side connector mounted on the lower tray and an opposite end to an eyelet attached to the end of the cord.
FIG. 8 is a side elevation view of the extension and eyelet shown in FIG. 7.

As shown in FIGS. 1, 3, and 5, cord 50 is round in cross-section and includes two stop members 56 and 58. The stop members 56 and 58 are affixed and spaced apart on the middle section 51 of cord 50. The stop members 56 and 58 are configured to press against or abut opposite sides of guide member 20 to prevent excessive side-to-side sliding movement of cord 50 through guide member 20.

In one embodiment, cord 50 is made of lightweight material with a fixed length. Two end connectors 53, 55 are formed on the cord's opposite end sections 52 and 54. The end connectors 53, 55 may be hooks or eyelets mounted on the cord's opposite end sections 52, 54, respective. The end connectors 53, 55 are configured to engage compatible securely, post-like side connectors 34, 36, formed or attached to the outside surfaces of the wing sections 30, 32 on the lower tray 25 (see FIGS. 1 and 6). At least one end connector 53 or 55 or both end connectors 53, 55 are configured slide through slot 21 formed on the guide member 20. The stop members 56, 58, are spaced 6 to 12 mm apart and separately attached to the cord.

Formed on the bottom surface 14 on the upper tray 12 is an optional rest plate 19 that extends downward and acts as a resting surface that keeps the wing of the upper and lower trays apart.

FIGS. 7 and 8 show optional extensions 60, used between the end connectors 53, 54 and the side connectors 34, 36 used to change the overall length of cord 50. Extension 60 may include a plurality of pegs 62 that can engage the end connector 53, 55. Formed on the opposite end of extension 60 is connection hole 63, which securely engages the side connector 34 or 36 on the lower tray 25.

Figure 9:
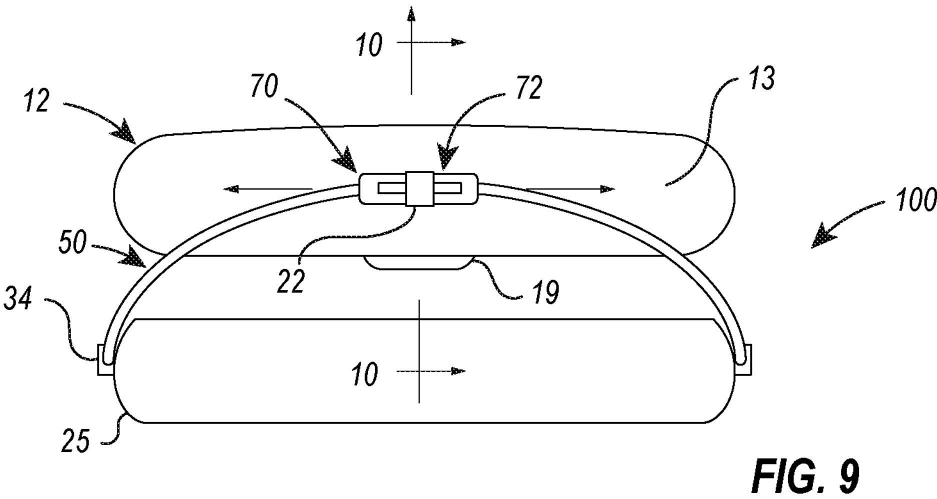
FIG. 9 is a front elevation view of an oral appliance with an upper tray and a lower tray, coupled with a cord with a slide member that engages a t-shaped cap attached to the upper tray's front surface.
Figure 10:
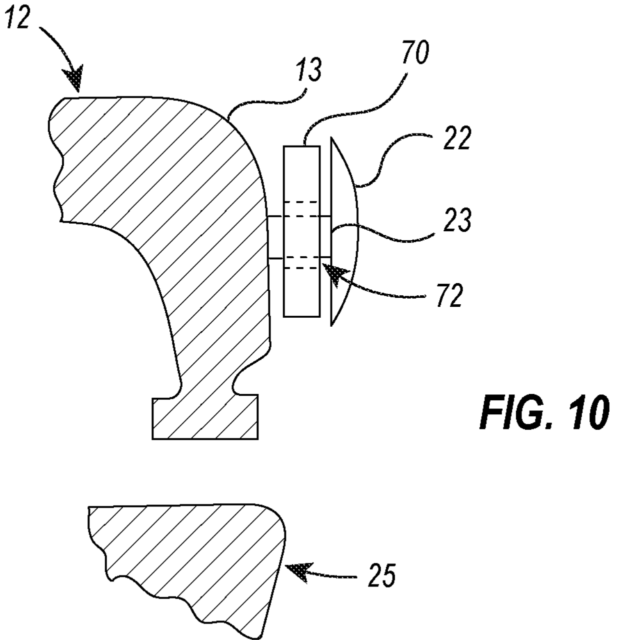
FIG. 10 is a sectional view taken along line 10-10 in FIG. 9.

FIG. 9 is a front elevational view of a second embodiment of the oral appliance, indicated by reference number 100 that also uses a modified upper tray 12 and a lower tray 25, coupled with a cord 50. The cord 50 includes a slide member 70 with a longitudinally aligned slot 72. The slot 72, approximately ⅛ in width and approximately ¼ inches in length, engages a post 23, shown more clearly in FIG. 10, and extends forward from the front surface 13' of the upper tray 12. Post 23 is slightly smaller than slot 72 and extends forward from the front surface 13', approximately ⅛ to 3/16 inches. Attached to post 23 is a retaining cap 22 that holds slide member 70 on the post 23. During use, slide member 70 moves back and forth over the post 23 approximately 1/16 to ⅛ inches to balance the pulling forces exerted on opposite sides of the upper tray 12. FIG. 10 is a sectional view taken along line 10-10 in FIG. 9.

Figure 11:
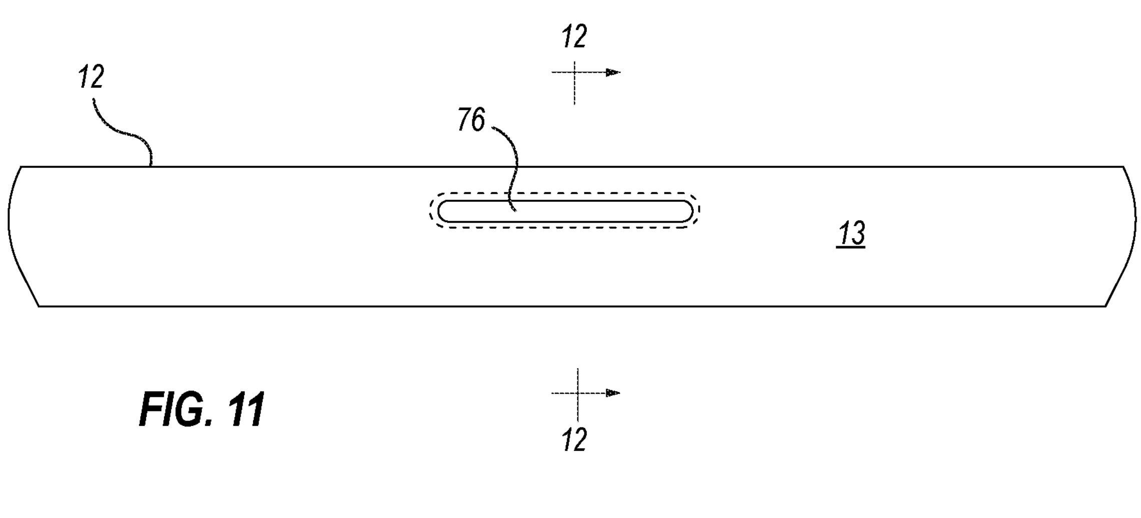
FIG. 11 is a front plan view of the upper tray with a curved slot on the front surface.
Figure 12:
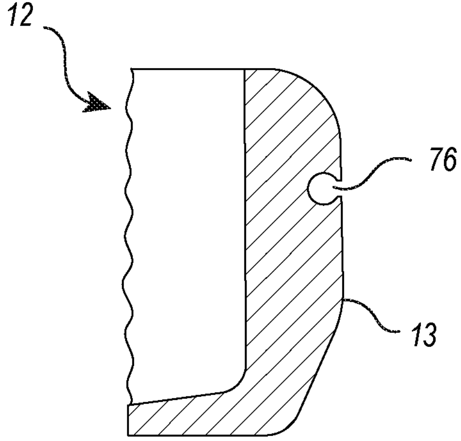
FIG. 12 is a sectional side elevation view of the upper tray taken along line 12-12 in FIG. 11.

FIGS. 11 and 12 show a curved slot 76 formed in the front surface 13 of the second modified upper tray 12. The curved slot 76 is an arc that matches the curvature of the round cord 50 when its opposite end connectors are attached to the side connectors.

Figure 13:
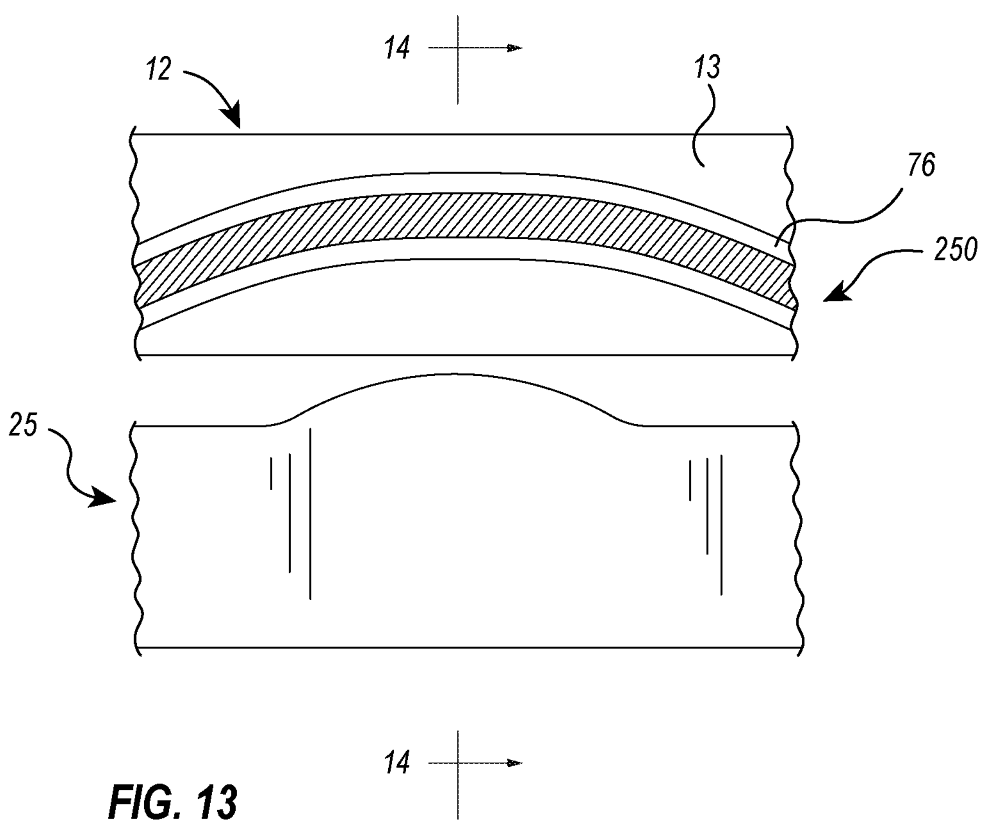
FIG. 13 is a partial front view of the upper and lower trays, showing a curved flat slot formed on the front surface of the upper tray with a flat cord placed inside a curved, flat slot.

FIG. 13 is a partial front view of the upper and lower trays 12, 25 showing a curved flat slot 76 formed on the front surface 13 of the upper tray 12. The curved flat slot 76 is configured to receive a flat cord 250. The curved flat slot 76 is an arc that matches the curvature of the flat cord 250 when its opposite end connectors are attached to the side connectors.

Figure 14:
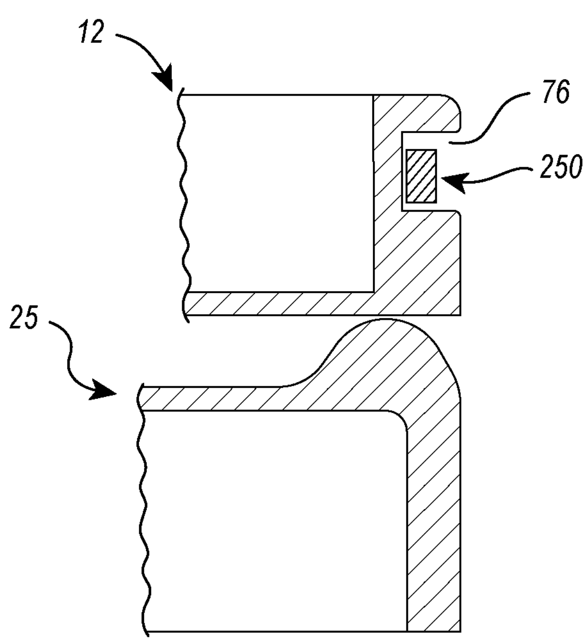
FIG. 14 is a sectional view taken along line 14-14 in FIG. 13.
Figure 15:
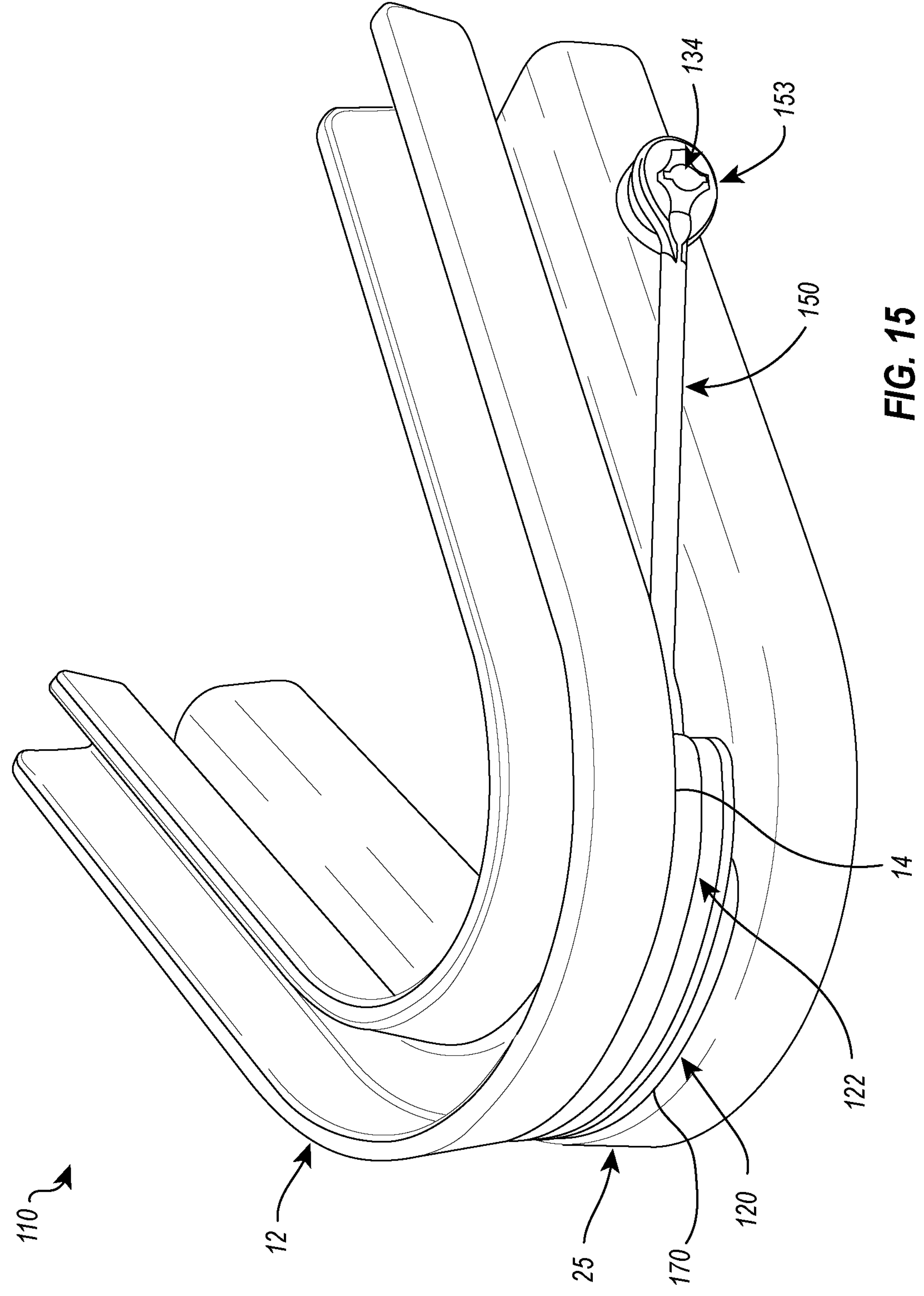
FIG. 15 is a side, perspective view of another embodiment of the oral appliance that uses a guide member attached to the front, lower surface of the upper tray and a rest plate formed or attached to the front upper surface of the lower tray.

FIG. 14 is a sectional view taken along line 14-14 in FIG. 13.

FIGS. 15-21 show a third embodiment of the oral appliance, denoted by reference number 110, that uses a cord 150 circular in cross-section similar to the cord 50 used in the first embodiment shown in FIG. 1-3. In the oral appliance 110, guide member 120 is attached to the bottom surface 14 of the upper tray 12. Guide member 120 is a curved structure and extends downward from the bottom surface 14. Guide member 120 includes a curved slot 122 on its front surface that captures the cord 150. Cord 150 has a width slightly smaller than slot 122, allowing cord 150 to slide freely horizontally in a side-to-side manner in guide member 120.

Figure 16:
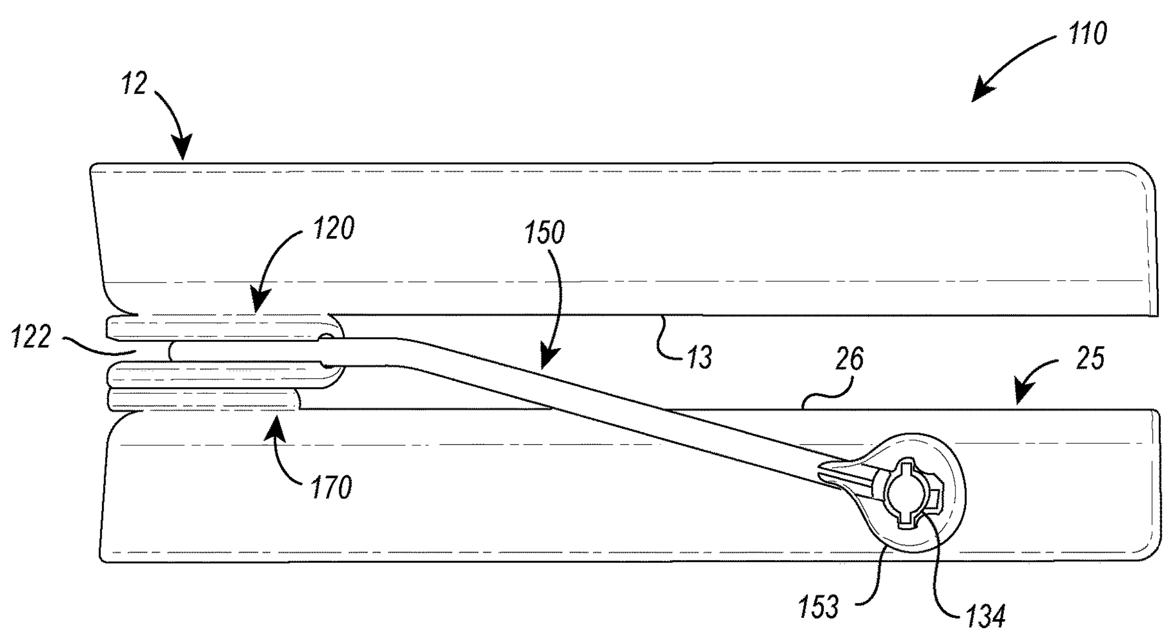
FIG. 16 is a left-side elevation view of the oral appliance shown in FIG. 15.
Figure 17:
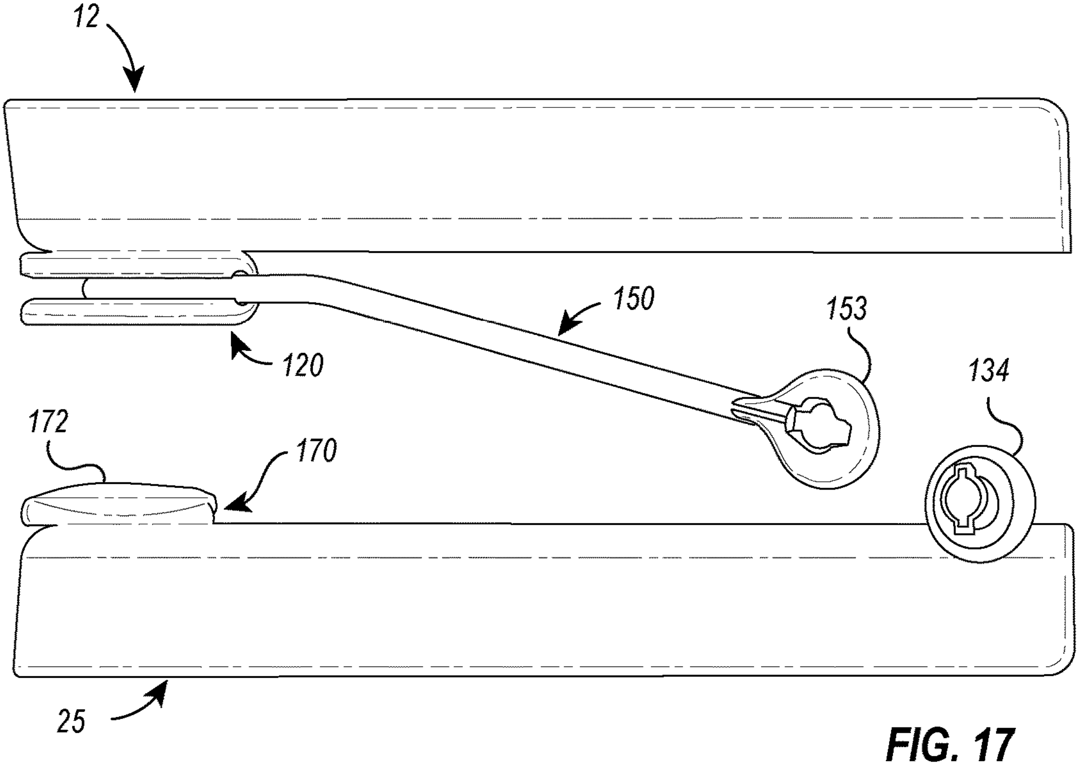
FIG. 17 is an exploded, left-side elevation view of the oral appliance shown in FIG. 15.
Figure 18:
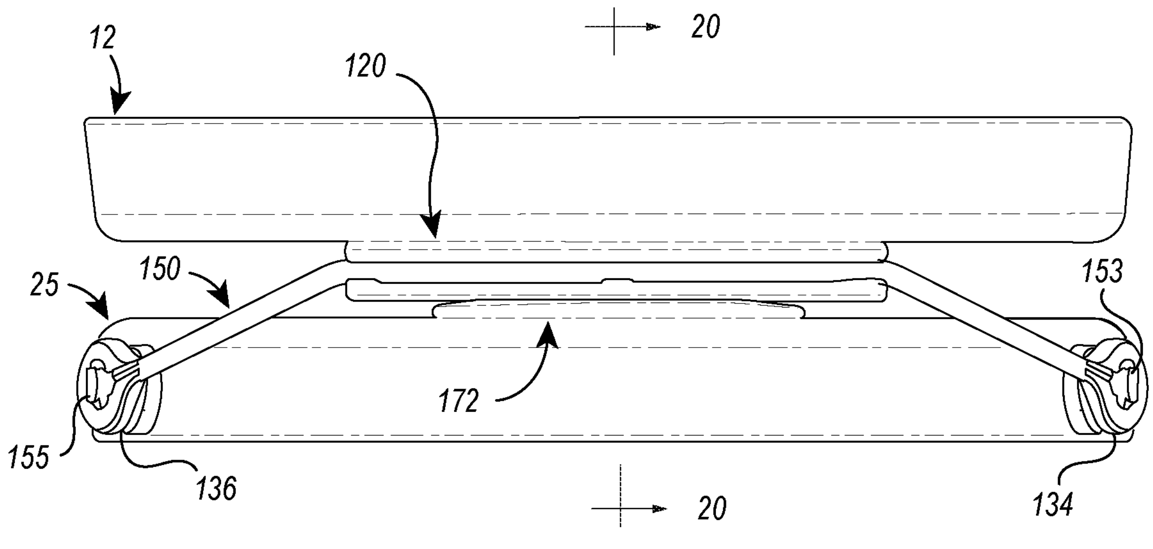
FIG. 18 is a front elevation view of the oral appliance shown in FIG. 15.
Figure 19:
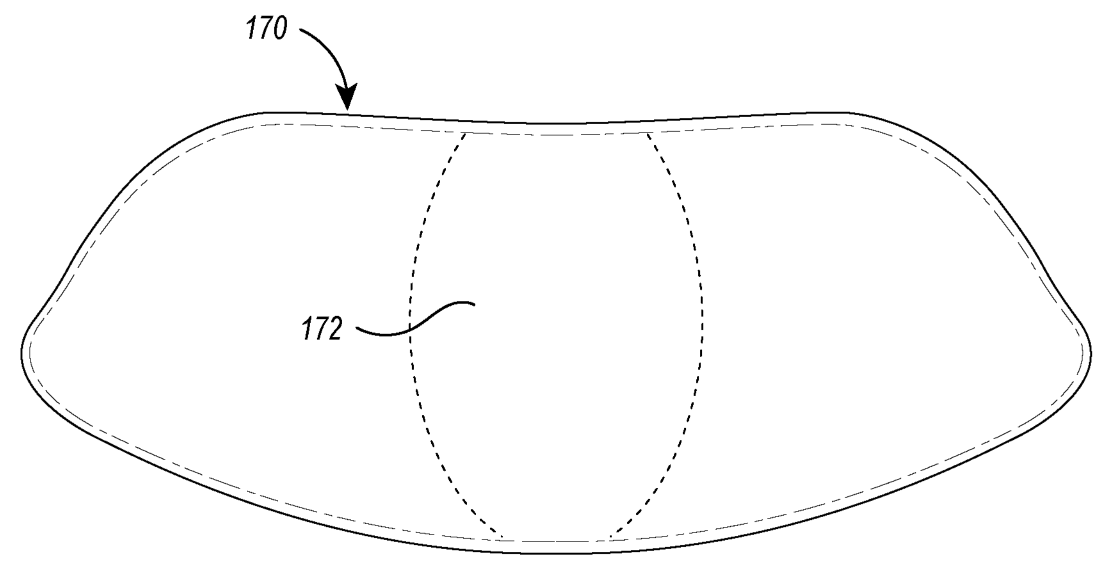
FIG. 19 is a top plan view of a rest plate.

FIGS. 16 and 17 show an optional rest plate 170 attached to the top surface 26 of the lower tray 25. During use, guide member 120 rests directly over the top surface of rest plate 170. As shown in FIGS. 18 19, the rest plate 170 may include a convex surface 172. Like the rest plate 19 shown FIGS. 1-3, the rest plate 170 is configured to hold the front curved surfaces of the upper and lower trays 12 and 25 apart 1 to 20 mm.

Figures 20, 21:
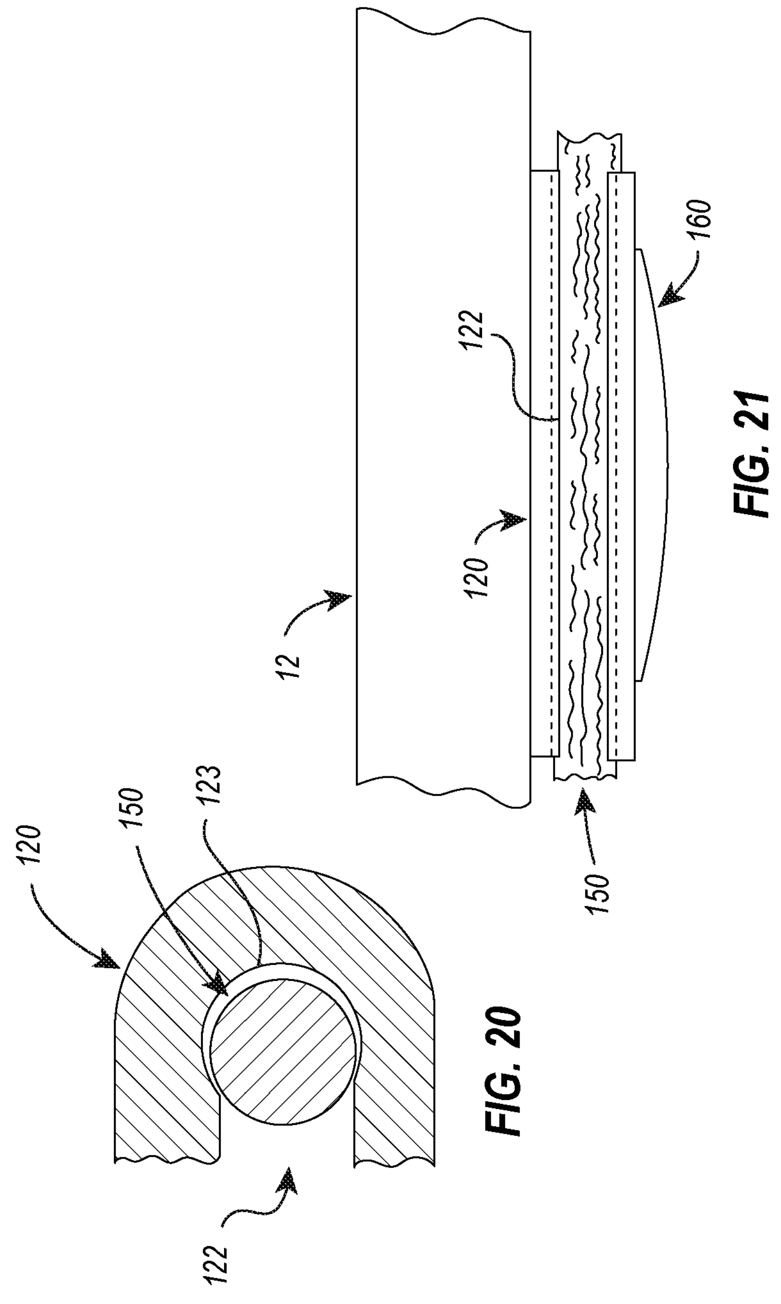
FIG. 20 is a sectional, side elevation view of the guide member taken along line 20-20 in FIG. 18, showing the round cord held inside an enlarged slot opening formed in the guide member.
FIG. 21 is a partial, enlarged front elevation view of the cord mounted inside the guide member.

FIG. 20 is a sectional side elevational view of guide member 120 with cord 150 held inside an enlarged circular area located on the inside surface of slot 122. FIG. 21 is a partial, enlarged front elevational view of the upper tray 12, showing cord 150 sliding inside slot 122 formed on guide member 120.

Figures 22, 23:
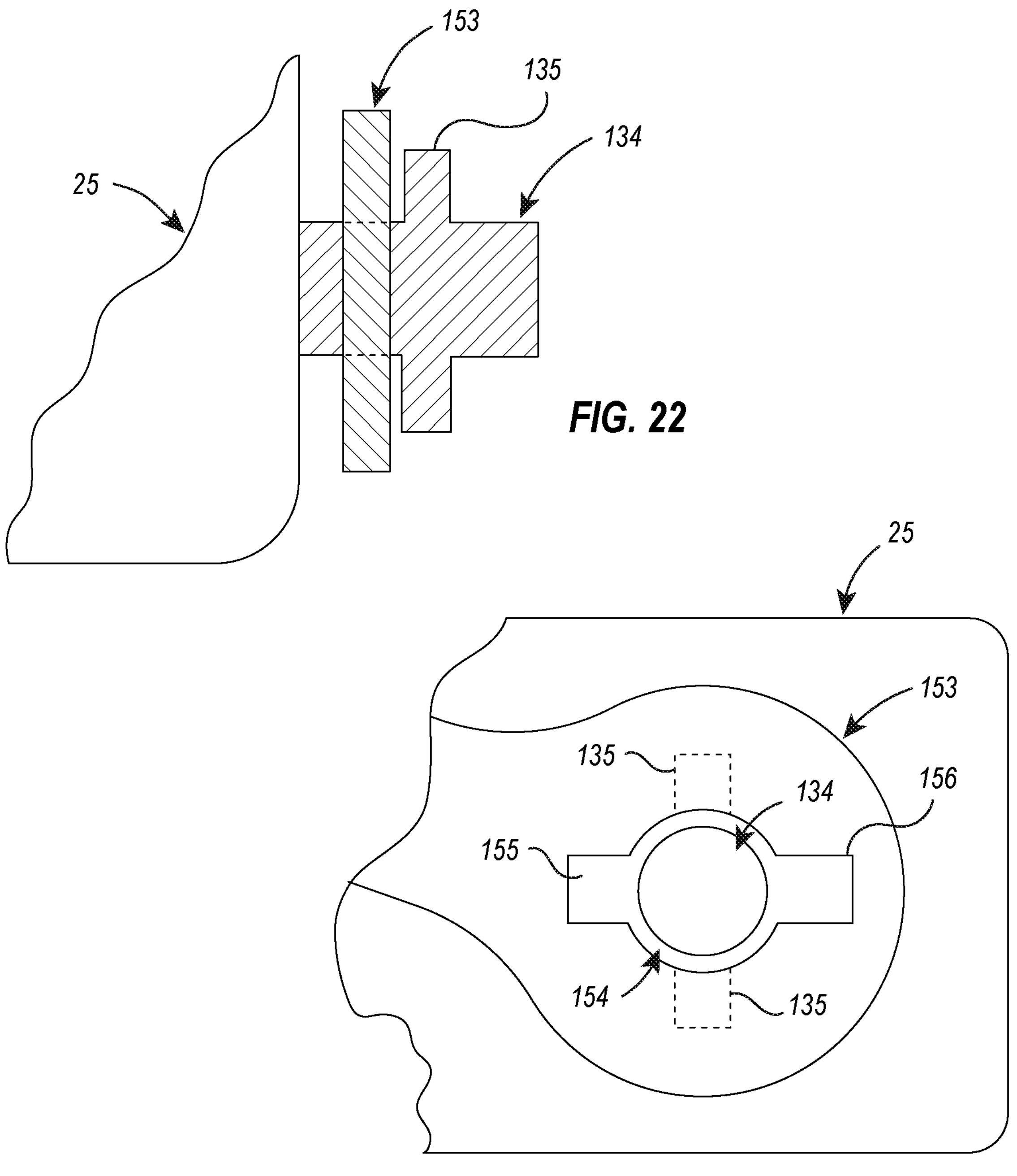
FIG. 22 is a side elevation view of a T-shaped side connector and a cord connected to the side connector.
FIG. 23 is a partial, side elevational view of the cord attached to the side connector.
Figure 24:
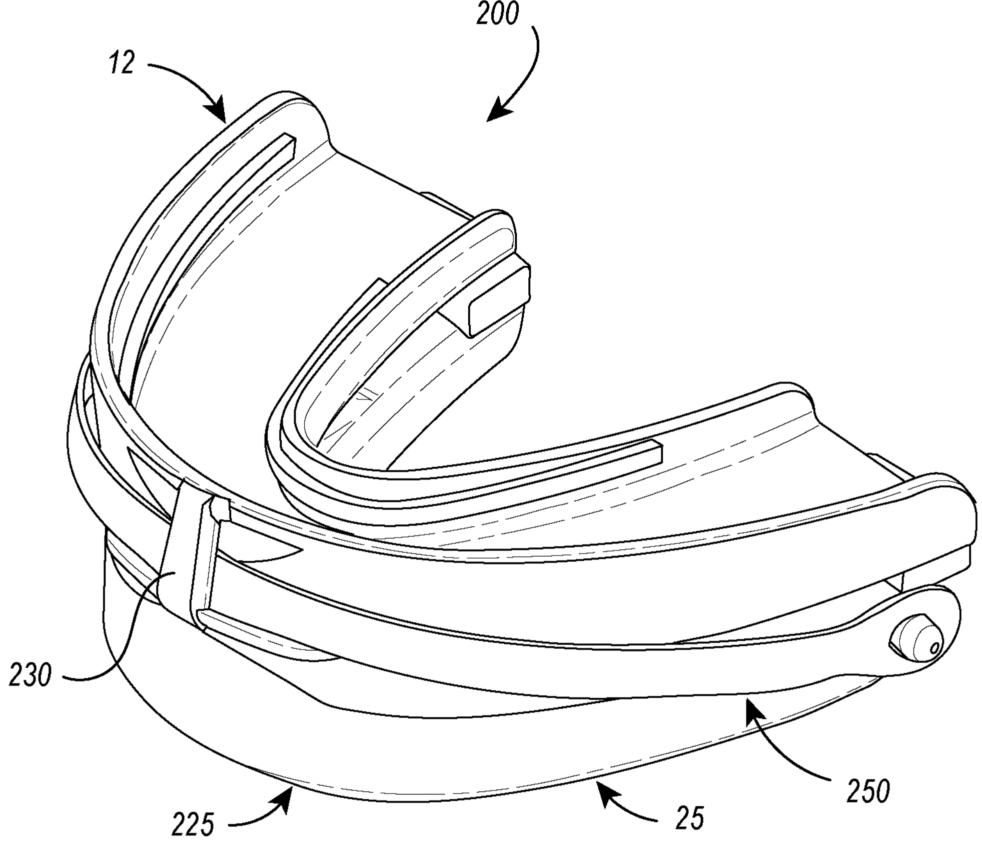
FIG. 24 is a top perspective view of a fourth embodiment of the oral appliance that includes a single vertical slot formed on the front surface of the upper tray and a flat cord that connects are its opposite ends to two connectors mounted on the outside surfaces of the lower tray.
Figure 25:
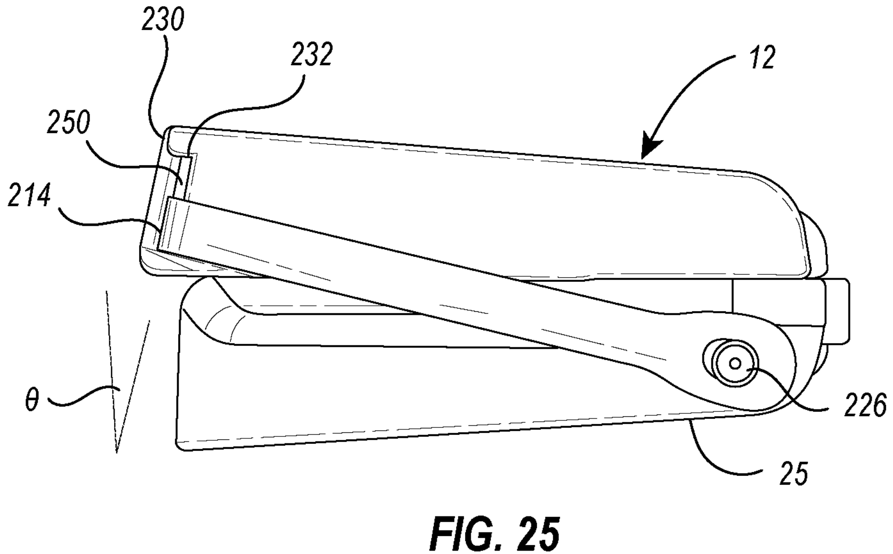
FIG. 25 is a left side elevation view of the oral appliance shown in FIG. 24.
Figure 26:
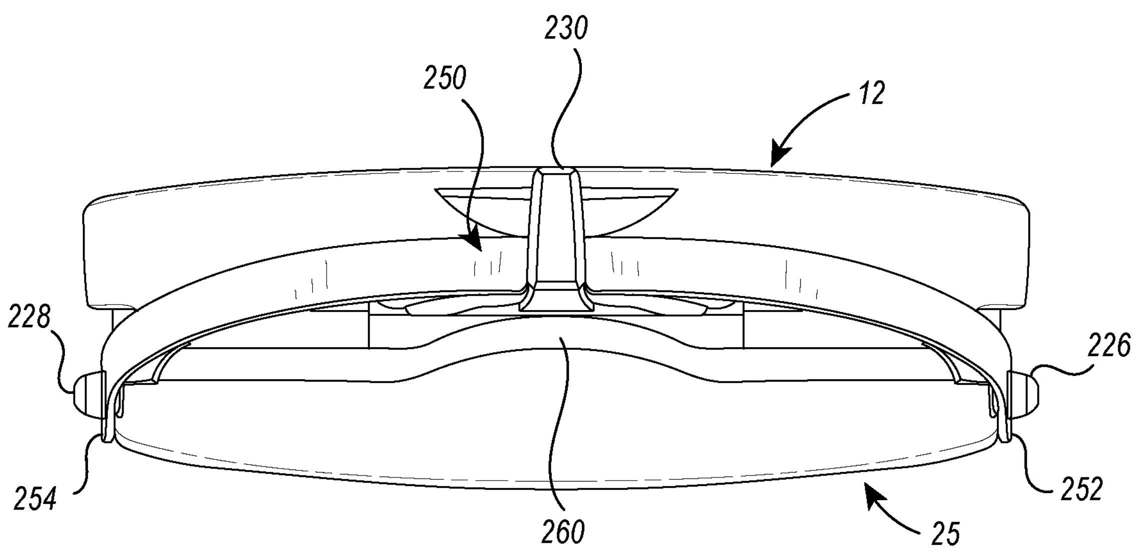
FIG. 26 is a front elevation view of the oral appliance shown in FIGS. 24 and 25.
Figure 27:
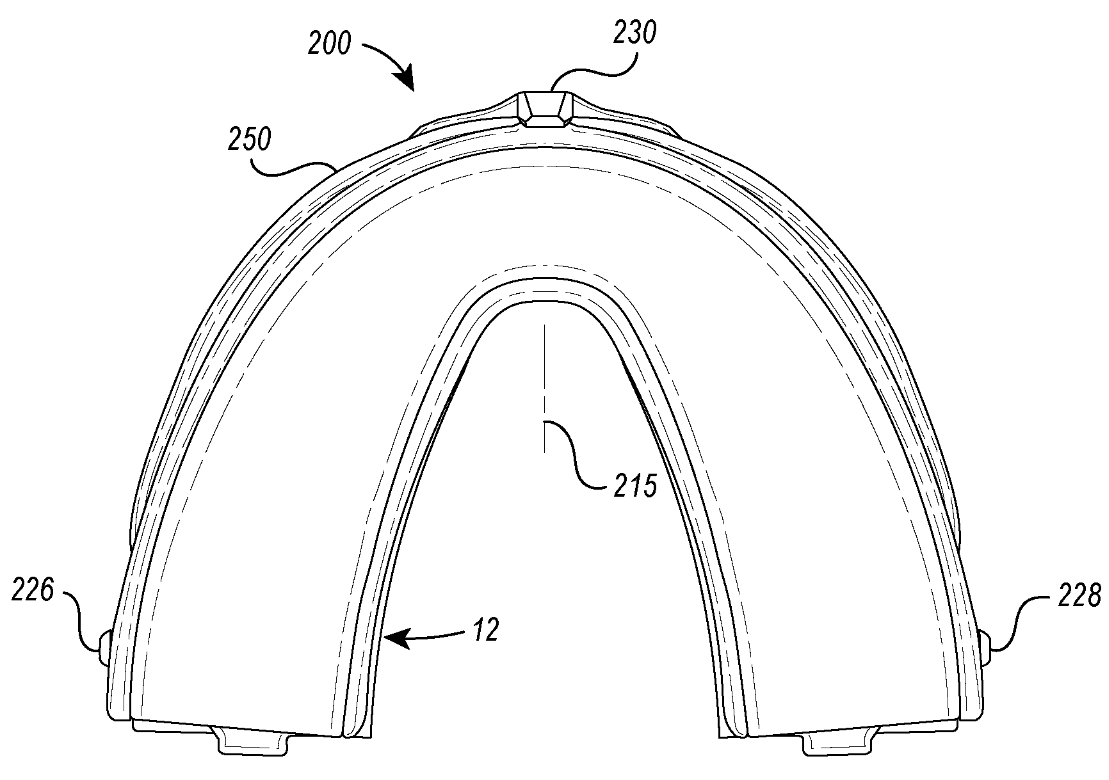
FIG. 27 is a top plan view of the oral appliance shown in FIGS. 24 and 25.
Figure 28:
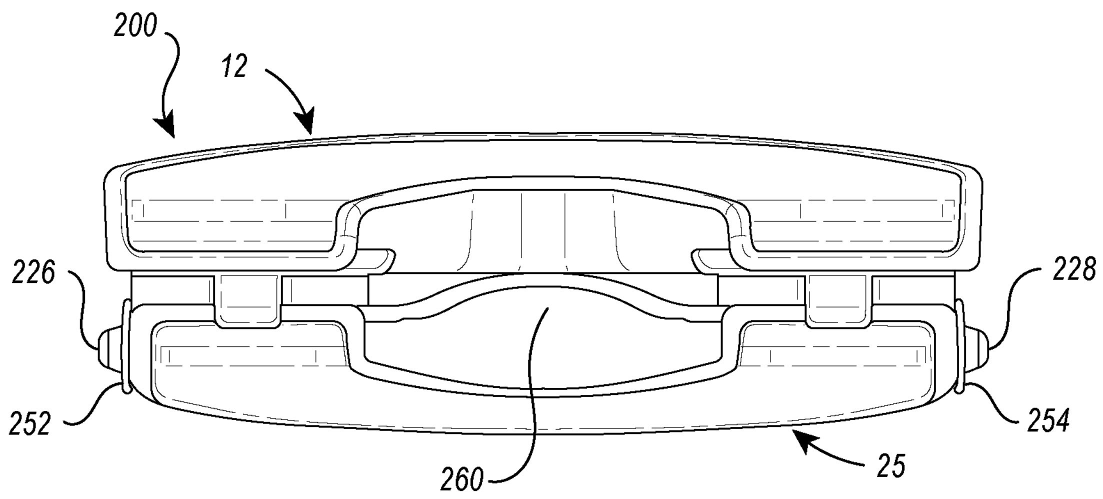
FIG. 28 is a rear elevation view of the oral appliance shown in FIGS. 24 and 25.

FIG. 22 is a partial side elevation view of the lower tray 25 with a T-shaped side connector 134 formed or attached to the outside surface of the wing sections on the lower tray 25. The side connector includes a post 134 with two opposite lateral ears 135. The ends of the cord 153 include a center bore 154 configured to receive post 134. Extending radially from the center bore 154 are two opposite slots 155 and 156. Lateral ears 135 are vertically aligned on post 134, so cord 153 and ears 135 act as a key and keyways that require rotation of approximately 90 degrees to attach or remove the cord 153 from the side connector 134.

FIG. 23 is a partial, side elevational view of cord 153 attached to the side connector.

Like the first embodiment shown in FIGS. 1-3, the oral appliance 110 may include an optional downward extending spacer 160 extending downward from the guide member 120, as shown in FIGS. 16, 17 and 19. When oral appliance 110 is worn, the spacer 160 holds the upper and lower trays 12 and 25 wing sections apart from 1 to 20 mm. The spacer 160 is a convex surface or bump in the embodiment shown. It should be understood that the spacer 160 may have other configurations, such as a post or wall.

It should be understood that the spacer 160 may be integrally formed on the bottom surface of guide member 120. Alternatively, spacer 160 may be formed on a separate structure, called a rest plate 162, that selectively attaches to the top surface 26 of the lower tray 25 directly under the guide member 120 as shown in FIG. 17. During manufacturing, the vertical thickness and length of the spacer 160 may vary so that the adjacent horizontal surfaces 13, 26 of the upper and lower trays 12, 25, respectively, are slightly spaced apart and parallel to accommodate different jaw configurations.

FIGS. 24-28 show a fourth embodiment of the oral appliance 200 that includes a single vertical slot 232 formed on the front surface of the upper tray 12 and a flat cord 250 that extends upward from the lower tray 25 and over the front surface 214 of the upper tray 12. The flat cord 250 is made of thin, material, such as plastic or nylon, that is resistant to stretching. Because the flat cord 250 is resistant to bending longitudinally, the front surface 214 of the upper tray 12 is slanted rearward from upper tray's vertical axis approximately 12 degrees (see FIG. 24). The angle of the front surface 214 is configured so that the longitudinal axis of the flat cord 250 is perpendicular to the front surface 214 when installed. In the embodiment shown, a forward extension 230 is formed along the upper tray's center axis 215. Formed inside extension 230, is the diagonal slot 232 measures approximately 8 mm in length and 4 mm in width. The inside surface of the front extension 230 extends forward from the front surface 214 of the upper tray, approximately 2.5 mm.

The flat cord 250 functions similarly to the round cord 50 used with the other embodiments. The flat cord 250 is approximately 0.5 to 1.0 mm thick and 15 to 20 mm wide. The slot 232 is slightly wider than the flat cord 250, enabling the flat cord 250 to side horizontally freely through the diagonal slot 232.

Formed on the opposite ends of the flat cord 250 are end connectors 252, 254, like the end connectors used in the embodiments described above. The end connectors 252, 254 are flat and slightly smaller than the length of the vertical slot 232, enabling the user to slide one end of the flat cord 250 through vertical slot 232.

Like the embodiment shown in FIGS. 13-21, an optional spacer in the form of a convex surface 260 may be formed on the top surface 226 of the lower tray 25 (shown) or on the bottom surface of the upper tray. The height of the convex surface 260 must be sufficient so that the trays are spaced apart when the trays 12 and 25 are worn. The convex surface 260 may be formed on a replacement rest plate attached to the upper or lower trays 12, 25. Also, the convex surface 260 may be made of material that can be cut to adjust the gap or spacing of the upper and lower trays 12, 25.

Figure 29:
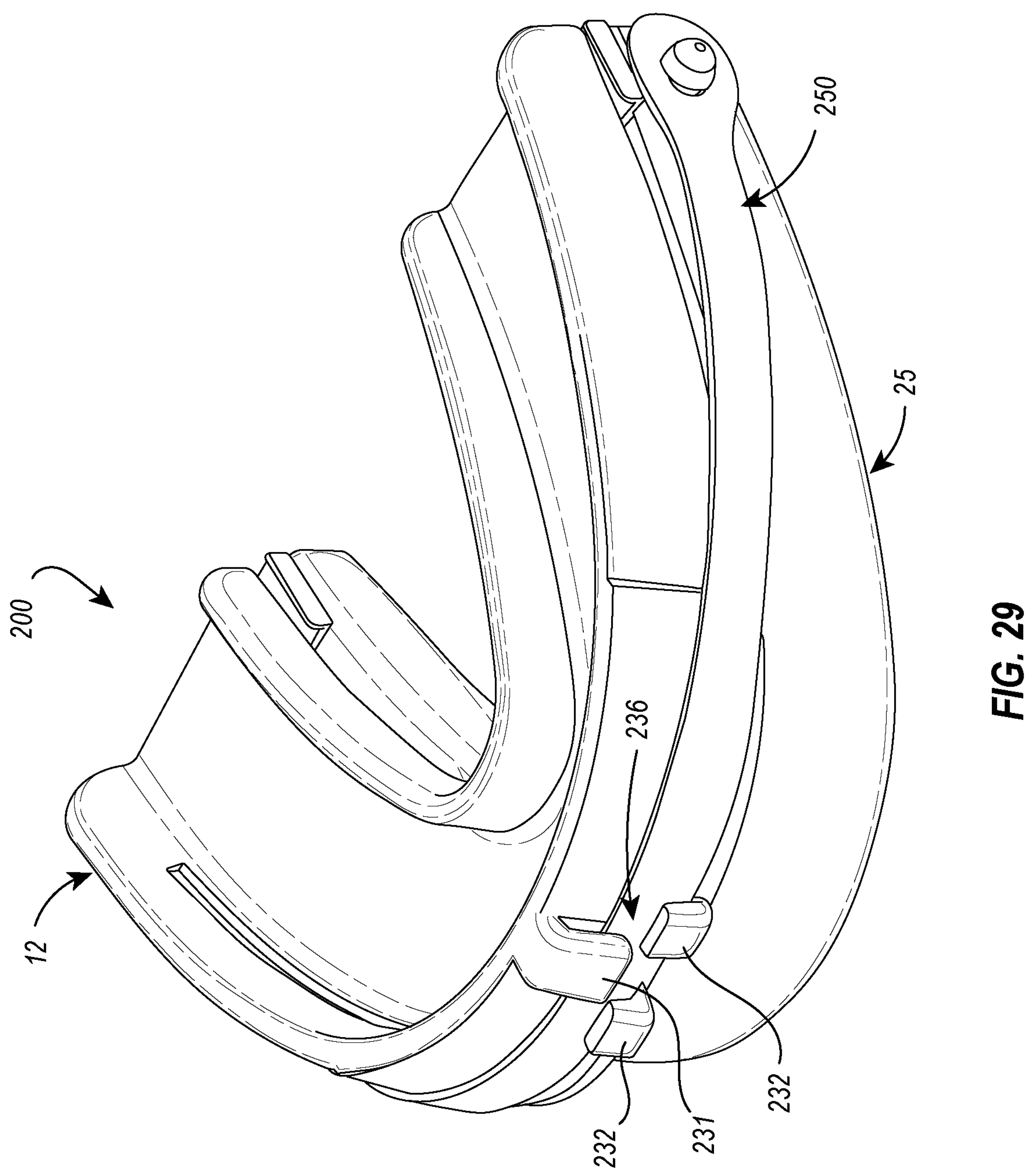
FIG. 29 is a top perspective view of the fourth embodiment of the oral appliance that uses a single downward lip and two upward lips formed on the front surface of the upper tray with a horizontal slot formed between the downward lip and the two upward lips and a flat cord extending into the slot with its opposite end connectors connecting to the side connectors on the lower tray.

FIG. 29 is a top perspective view of another embodiment of the oral appliance 200 that uses a single downward lip 231 and two upward lips 232 formed on the front surface of the upper tray 12. Lips 232 are located on opposite sides of lip 231. A horizontal slot 236 is formed between the front surface of the upper tray 12 and the downward lip 231 and the two upward lips 232. Slot 236 is configured to receive a flat cord 250 extending upward from the two side connectors on the lower tray 25.

Figure 30:
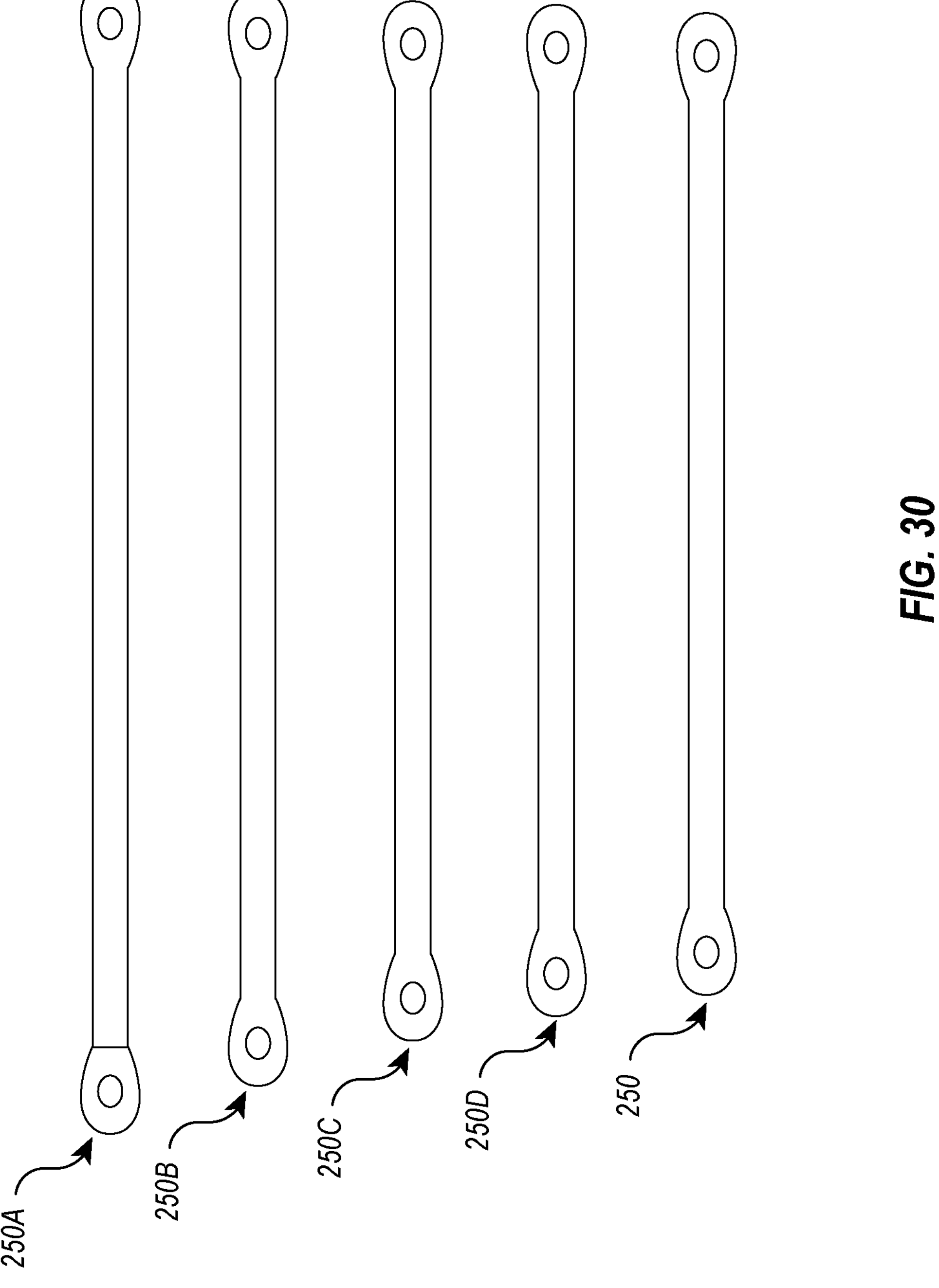
FIG. 30 shows a set of five exchangeable flat cords.

FIG. 30 shows a set of five exchangeable flat cords, 250, 250A, 250B, 250C, and 250D, varying in length distributed and used with the appliance. The longest cord (250A) is usually first selected and attached to the side connectors during use. The upper and lower trays are then inserted over the upper and lower user's dental arches. The user then sleeps with the appliance and monitors their sleep to determine if snoring has been eliminated. If snoring has not been eliminated, then the next shorter cord (250B), is attached to the appliance and inserted into the bridges. The user then sleep with the appliance and monitors their sleep for snoring. The above steps are repeated until snoring is eliminated. It should be understood that the use of shorter flat cords may cause discomfort. In discomfort occurs, the user is advised to select the next flat cord in the set of cords that is effective in reducing snoring and is comfortable.

In compliance with the statute, the invention described herein has been described in language that is more or less specific to structural features. It should be understood, however, that the invention is not limited to the specific features shown since the means and construction shown are comprised only of the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. An oral appliance configured to urge a user's mandibular arch forward relative to said user's maxillary arch, said oral appliance, comprising:

a U-shaped upper tray configured to conform to a user's maxillary arch, said U-shaped upper tray includes a curved front surface, a curved bottom surface and defines a center axis;

a U-shaped lower tray configured to conform to said user's mandibular arch, said U-shaped lower tray includes a curved front surface, a curved top surface, and a pair of opposed wing sections;

wherein the U-shaped upper tray includes a cord receiver positioned on said curved bottom surface of said U-shaped upper tray;

a spacer positioned between the U-shaped upper tray and the U-shaped lower tray, wherein the spacer is formed on said lower tray or on said upper tray, said spacer configured to keep said curved front surface on said U-shaped upper tray and said curved front surface of said U-shaped lower tray apart during use; and a cord configured to slidably engage within the cord receiver of the U-shaped upper tray and to pivotably engage with the pair of opposed wing sections of the U-shaped lower tray, wherein said cord includes a middle section and a pair of opposed end sections, each opposed end section having a coupler, said cord having a fixed length so when, during use, said middle section slidably engages with the cord receiver of the U-Shaped upper tray and pivotably engages with the pair of opposed wing sections of the U-Shaped lower tray, to allow the cord to self-adjust relative to the U-Shaped upper tray and equally apply upward diagonal forces to said pair of opposed wing sections of said U-shaped lower tray.

2. The oral appliance, as recited in claim 1, wherein said spacer defines a convex surface.

3. The oral appliance, as recited in claim 2, wherein said cord receiver comprises a guide member.

4. The oral appliance, as recited in claim 1, wherein said cord receiver is aligned with said center axis of said U-shaped upper tray.

5. The oral appliance, as recited in claim 1, wherein the spacer is integrally formed with the cord receiver.

6. An oral appliance configured to urge a user's mandibular arch forward relative to said user's maxillary arch, comprising:

a U-shaped upper tray configured to conform to the user's maxillary arch, said upper tray includes a curved front surface, a curved bottom surface, and two posterior sections;

a U-shaped lower tray configured to conform to the user's mandibular arch, said lower tray includes a curved front surface and two opposite wing sections;

a guide member extending downwardly from said curved front bottom surface of said U-shaped upper tray;

a spacer positioned between said U-shaped upper tray and said U-shaped lower tray, wherein the spacer is defined by said U-shaped upper tray or said U-shaped lower tray; and a cord configured to slide freely inside said guide member, said cord defining opposed ends and having a coupler positioned at each of the opposed ends of said cord, each said end coupler configured to couple the respective end of the cord with a corresponding one of the opposite wing sections of said U-shaped lower tray, whereby when said cord is inserted into said guide member and said end couplers are attached to the opposite wing sections of said U-shaped lower tray, said cord is freely slidable through said guide member to automatically balance the pulling forces exerted by said cord on said opposite wing sections of said U-shaped lower tray.

7. The oral appliance, as recited in claim 6, wherein the spacer is defined by the U-shaped upper tray and extends downward from the guide member to keep said posterior sections of the U-shaped upper tray and said opposite wing sections of the U-shaped lower tray apart from each other when said appliance is worn.

8. The oral appliance, as recited in claim 7, wherein said spacer defines a convex surface.

9. The oral appliance, as recited in claim 6, wherein said cord has a fixed length and is made of non-elastic material.

10. The oral appliance, as recited in claim 6, wherein the spacer is integrally formed with the guide member.

11. An oral appliance, comprising;

a U-shaped upper tray configured to fit over the maxillary arch of a wearer, said U-shaped upper tray includes a curved anterior surface and a curved bottom surface;

a U-shaped lower tray configured to fit over the mandibular arch of the wearer, said U-shaped lower tray includes two opposite wings;

an integrally formed spacer and cord guide, the integrally formed spacer and cord guide extending from the curved bottom surface of the U-shaped upper tray between the U-shaped upper tray and the U-shaped lower tray;

a cord defining two opposed end regions each configured to couple with the opposite wings of said lower tray, said cord defining a central region configured to slide freely inside said cord guide and to self-adjust to exert balanced pulling forces on the opposite wings of said U-shaped lower tray, thereby maintaining the opposite wings of said U-shaped lower tray under and spaced apart from said U-shaped upper tray while the wearer sleeps.

* * * * *